United States Patent [19]
Sobotta et al.

[11] Patent Number: 5,627,272
[45] Date of Patent: May 6, 1997

[54] PROCESS FOR PREPARING SUGAR ACETONIDES

[75] Inventors: Rainer Sobotta, Ingelheim am Rhein; Franz Dietrich Klinger, Griesheim; Heinrich Schneider, Ingelheim am Rhein, all of Germany

[73] Assignee: Boehringer Ingelheim KG, Ingelheim am Rhein, Germany

[21] Appl. No.: 301,099

[22] Filed: Sep. 6, 1994

[30] Foreign Application Priority Data

Sep. 10, 1993 [DE] Germany ............... 43 30 701.9

[51] Int. Cl.$^6$ ........................................... C07H 1/00
[52] U.S. Cl. ................. 536/18.6; 536/18.4; 536/18.5; 536/55.1; 536/63
[58] Field of Search ................. 536/18.6, 18.5, 536/55.1, 63

[56] References Cited

U.S. PATENT DOCUMENTS

| | | | |
|---|---|---|---|
| 4,491,668 | 1/1985 | Ikawa et al. | 549/315 |
| 4,567,282 | 1/1986 | Mizuno et al. | 549/450 |
| 5,220,002 | 6/1993 | Akiyama | 536/187 |

FOREIGN PATENT DOCUMENTS

| | | |
|---|---|---|
| 0191464 | 8/1986 | European Pat. Off. . |
| 4227022 | 2/1994 | Germany . |

OTHER PUBLICATIONS

T.W. Greene and P.G.M. Wuts, *Protective Groups in Organic Synthesis* (John Wiley & Sons, Inc., New York) pp. 88–89 (1991).

*Primary Examiner*—James O. Wilson
*Attorney, Agent, or Firm*—Robert P. Raymond; Wendy E. Rieder; Alan R. Stempel

[57] ABSTRACT

A method of preparing sugar acetonides, such as for example 1,2:5,6-Di-O-isopropylidene-α-D-glucofuranose, by reacting the corresponding sugar, e.g. D-(+)-glucose, with acetone in the presence of a Lewis acid and a carboxylic acid derivative of general formula

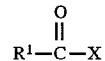

wherein X is a leaving group which may be readily replaced by a hydroxyl group.

15 Claims, No Drawings

PROCESS FOR PREPARING SUGAR ACETONIDES

The present invention relates to an improved process for preparing sugar acetonides, such as, for example 1,2-5,6-diacetone-D-glucose (1,2:5,6-di-O-isopropylidene-α-D-glucofuranose)

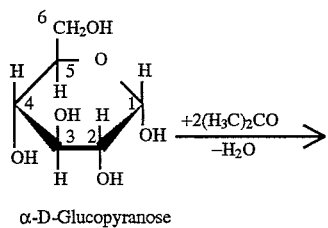

α-D-Glucopyranose

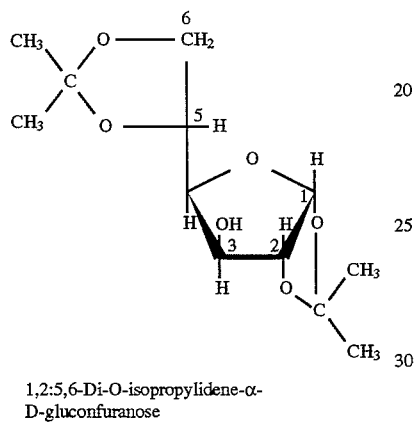

1,2:5,6-Di-O-isopropylidene-α-D-gluconfuranose from the corresponding sugars—in this particular example D-glucose—and acetone in the presence of compounds of general formula:

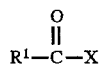

wherein X functions as a leaving group which can be readily replaced by a hydroxy group and, preferably, is selected from the group consisting of

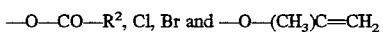

wherein $R^1$ and $R^2$ independently of each other may denote methyl, ethyl, propyl, isopropyl, butyl (branched or unbranched), pentyl (branched or unbranched) and hexyl (branched or unbranched). The starting materials used for the purposes of the present invention are chiefly monosaccharides such as D-galactose, D-glucose, L- and D-arabinose, fructose, D-mannose, sorbose, D-xylose, D-ribose, D-mannitol or L-ascorbic acid, or oligosaccharides or suitable polysaccharides, provided that they satisfy the requirement of having two sterically adjacent hydroxyl groups in the cis-position.

Diisopropylidene derivatives of the sugars, such as for example 1,2-5,6-diacetone-D-glucose, are inter alia central intermediate products for numerous other sugar derivatives or glucose derivatives which are of major importance in pharmaceutical preparations, among other things. 2-Deoxy-D-riboseanilide or amiprilose may be mentioned by way of example.

In addition, 1,2-5,6-diacetone-D-glucose may be used as a chiral ligand in complexes which permit enantioselective reactions [F. D. Klingler and M. Psiorz, Chimicaoggi 1992, 47].

This central role of 1,2-5,6-diacetone-D-glucose is responsible for the fact that the annual requirement of this intermediate product runs to many tons. It is generally known from the prior art that monosaccharides which contain two sterically adjacent OH-groups in the cis-position can be reacted with aldehydes or ketones in the presence of sulphuric acid, zinc chloride or phosphorus(V)-oxide to obtain the corresponding acetals (E. Fischer, 1895).

Thus, for example, 1,2:5,6-di-O-isopropylidene-α-D-glucofuranose (diacetone-α-D-glucose) can be obtained by reacting D-glucose with acetone in the presence of sulphuric acid. In order to achieve high turnover the water resulting from the ketalisation must be bound or removed from the reaction mixture.

It is also known from the prior art to prepare diacetone glucose in the presence of acidically reacting catalysts such as Lewis acids, for example complex compounds of boron trifluoride, aluminium halides, such as aluminium(III)-chloride or -bromide, tin salts or halides of rare earths.

Other catalysts known from the prior art include iodine, gypsum and molecular sieves. However, the use of catalysts which have hitherto been regarded as suitable has serious disadvantages, and not only in reactions on an industrial scale, of which the following are mentioned by way of example:

when using inorganic acids or phosphorus pentoxide, large amounts of these agents have to be used, which on the one hand allows only a small throughput and on the other hand involves major problems of disposal of the salts resulting from the neutralisation which is required afterwards;

when iodine is used large quantities of solvent are necessary, which again permits only a small throughput;

when an additional solvent is used which is capable of forming an azeotrope with water, the volume of the reactor vessel has to be increased further and also the use of an entraining agent, such as pentane, for example, results in the lowering of the boiling point, thus limiting the reaction temperature and extending the reaction time accordingly;

the use of solid catalysts also presents problems because of the caramelization which occurs and furthermore, the recovery and re-use of ion exchangers involves very great expense;

In addition, many reactions have the disadvantage that the side reactions, such as self-condensation of acetone, the extent of which depends on the particular reaction conditions, in some cases produce tarry by-products which on the one hand affect the efficacy of the catalyst and on the other hand lead to undesirable contamination of the reaction product which can sometimes only be removed by chromatographic purification.

The aim of the present invention is therefore to provide a process for preparing sugar acetonides which do not have the disadvantages known from the prior art and which makes the desired diisopropylidene derivatives such as 1,2-5,6-diacetone-D-glucose or diacetone-D-mannose available in high yields.

According to the invention, this is achieved by reacting the sugar with or in acetone in the presence of a Lewis acid, preferably boron trifluoride etherate and a carboxylic acid derivative of general formula

wherein X functions a leaving group which can be readily replaced by a hydroxyl group and, preferably, is selected from the group consisting of

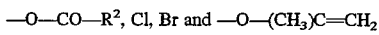

wherein $R^1$ and $R^2$ independently of each other may denote methyl, ethyl, propyl, isopropyl, butyl (branched or unbranched), pentyl (branched or unbranched) and hexyl (branched or unbranched).

The preparation process according to the invention has the advantage over the processes known from the prior art that it does not cause any waste products which are difficult to dispose of. Moreover, the process according to the invention uses a relatively small volume of solvent.

In order to carry out the process the (anhydrous) sugar is placed in the reaction vessel, suspended in acetone and mixed with the carboxylic acid derivative and with a Lewis acid. Suitable Lewis acids are known from the prior art; they include, for example, complex compounds of boron trifluoride, aluminium halides, tin salts and halides of rare earths. Preferably, boron trifluoride etherate is used as the Lewis acid. Then the reaction solution is heated to a temperature in the range from 40° to 58° C., preferably to reflux temperature (when acetic anhydride is used this will be about 58° C.) over a period of 4 to 8 hours, preferably 6 hours, during which a colourless reaction solution is formed. After the reaction has ended the mixture is cooled and a dilute aqueous solution of a basically reacting compound of an alkali or alkaline earth metal, e.g. a dilute aqueous solution of an alkali or alkaline earth metal hydroxide, preferably sodium hydroxide, is added, with stirring and cooling.

Then the unreacted acetone is removed by distillation, preferably under reduced pressure, and the distillation residue is combined with an extracting agent which is inert under the reaction conditions described, e.g. an aliphatic or aromatic hydrocarbon, preferably toluene.

The aqueous phase is extracted exhaustively, and the resulting diacetone sugar is precipitated from the combined extracts, optionally with the addition of a precipitating agent, preferably cyclohexane, at elevated temperature, which is in the range from 50° to 60° C., for example, preferably in the range from 50° to 55° C., and optionally with cooling. The crystals precipitated are isolated and optionally washed with a suitable solvent, preferably cooled cyclohexane, and then dried at elevated temperature, preferably at 40° C., in a circulating air dryer until a constant weight is achieved.

The objectives described herein before are achieved by means of the processes described in the following example. Various other embodiments of the process will be apparent to anyone skilled in the art from the present description. However, it is expressly pointed out that the example and the related description are given solely as an illustration and description and should not be regarded as restricting the invention. In particular, it is pointed out that the synthesis sequences described in the examples for the preparation of 1,2:5,6-Di-O-isopropylidene-α-D-glucofuranose and diacetone-D-mannose can also be applied to the preparation of other isopropylidene sugars. Examples of starting materials which might be used include the following additional monosaccharides: D-galactose, L- and D-arabinose, fructose, sorbose, D-xylose, D-ribose, D-mannitol and L-ascorbic acid.

EXAMPLE 1

3.78 kg (20.98 mol) of anhydrous D-(+)-glucose are placed in a dried reaction vessel under inert gas and suspended in 74 liters of acetone. Then 4.28 kg (41.92 mol) of acetic acid anhydride and 31 ml of borontrifluoride etherate are added. The reaction mixture is then heated to a reflux temperature of 58° C. over a period of six hours. Then the clear colourless reaction mixture is cooled to ambient temperature (about 20° C.). The reaction mixture treated in this way is added to a solution of 3.36 kg of sodiumhydroxide in 16.8 liters of demineralised water, the temperature of the reaction mixture being maintained below 35° C. by cooling. The acetone or the volatile constituents of the reaction mixture are distilled off from the mixture under a weak vacuum at a sump temperature of about 45° C.

After distillation, the distillation residue is extracted exhaustively with toluene.

The combined organic extracts (approximately 24 liters) are evaporated down to about 9 liters in vacuo and 14.5 liters of cyclohexane are added and the mixture is stirred for about 15 minutes at a temperature in the range from 50° to 55° C., during which time a clear yellow solution is formed.

Then the solution is stirred for one hour at a temperature of about 40° C., whereupon crystallisation occurs. The crystal suspension is cooled to about 10° C. and then stirred for about 1.5 hours at a temperature in the range from 2° to 4° C.

The resulting crystal slurry is filtered through a filter having a filling chamber and the filter cake is washed three times, each time with 400 ml of cooled cyclohexane. The residue remaining is then dried at 40° C. in a circulating air dryer. In this way, 2.956 kg (53% of theory) of the 1,2-5, 6-diacetone-D-glucose are obtained.

EXAMPLE 2

3.00 kg of anhydrous D-(+)-mannose are placed in a dried reaction vessel under inert gas and suspended in 42 liters of acetone. Then 28 g of borontrifluoride etherate are added. The reaction mixture is then heated to a reflux temperature of 58° C. and 2.5 kg of acetic anhydride are added within a period of one hour. Then the reaction mixture is heated to a reflux temperature over a period of 5 hours and approximately half the acetone originally put in is distilled off. The now clear, colourless reaction mixture is cooled to a temperature of 10° C. and then 12.3 liters of 25% sodiumhydroxide solution are added, whilst the pH of the reaction mixture should be at least 8 after the addition of the sodiumhydroxide solution. The acetone or the highly volatile constituents of the reaction mixture are distilled off from the reaction mixture under a weak vacuum.

After distillation is complete, the distillation residue is combined with toluene at a temperature of 65° C. and the organic phase is separated off and extracted with toluene.

The combined organic extracts are concentrated by evaporation in vacuo and filtered through a heated pressure filter at a temperature of about 70° C. Then the filter residue is washed twice with 0.5 liters of toluene. During the subsequent cooling period, crystallisation starts at about 50° C. After cooling to a temperature in the range from 5° to 7° C. a crystal slurry is formed which is suction filtered. The material obtained by filtering is then dried in a vacuum or circulating air dryer at a temperature in the range from 40° to 45° C.

In this way, 4.40 kg (67.7% t.q. based on the mannose put in) of diacetone-D-mannose are obtained.

What is claimed is:

1. A process for preparing an acetonide of a monosaccharide comprising the steps of
   (a) reacting a monosaccharide with acetone in the presence of a Lewis acid and a carboxylic acid derivative of the formula

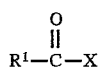

wherein X is a leaving group and $R^1$ is methyl, ethyl, propyl, isopropyl, butyl, pentyl, or hexyl to produce a reaction mixture;
   (b) cooling the reaction mixture;
   (c) contacting the cooled reaction mixture produced in step (b) with a dilute aqueous solution of an alkali or alkaline earth metal to form a solution;
   (d) extracting the solution produced in step (c) with an aliphatic or aromatic hydrocarbon to produce a combined extract; and
   (e) isolating the acetonide of a monosaccharide from the combined extract of step (d).

2. The process according to claim 1, wherein the monosaccharide is selected from the group consisting of D-glucose, D-galactose, L-arabinose, D-arabinose, fructose, D-mannose, sorbose, D-xylose, D-ribose, D-mannitol and L-ascorbic acid.

3. The process according to claim 1, wherein the monosaccharide is D-glucose.

4. The process according to claim 1 or 3, wherein X is selected from the group consisting of

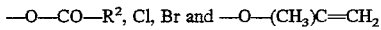

and $R^1$ and $R^2$ are independently methyl, ethyl, propyl, isopropyl, butyl, pentyl or hexyl.

5. The process according to claim 1 or 3, wherein the carboxylic acid derivative is acetic anhydride.

6. The process according to claim 1 or 3, wherein the reaction of step (a) is carried out at a temperature in the range of 40° to 58° C.

7. The process according to claim 6, wherein the temperature is in the range of 50° to 55° C.

8. The process according to claim 1 or 3, wherein the dilute aqueous solution of an alkali or alkaline earth metal is a dilute sodium hydroxide solution.

9. The process according to claim 1 or 3, wherein step (e) consists essentially of heating the combined extract of step (d) to a temperature in the range of 50° to 60° C., filtering the heated combined extract, then crystallizing the acetonide of a monosaccharide.

10. The process according to claim 1 or 3, wherein the aliphatic or aromatic hydrocarbon is toluene.

11. The process according to claim 1 or 3, wherein step (e) consists essentially of heating the combined extract of step (d) then combining the heated combined extract with a precipitating agent.

12. The process according to claim 11, wherein the precipitating agent is cyclohexane.

13. A process for preparing 1,2-5,6-diacetone-D-glucose from a monosaccharide comprising the steps of:
    (a) reacting D-glucose with acetone in the presence of a Lewis acid and a carboxylic acid derivative of the following formula

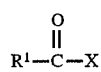

wherein X is a leaving group and $R^1$ is methyl, ethyl, propyl, isopropyl, butyl, pentyl or hexyl at a temperature in the range of 40° to 58° C.;
    (b) cooling the reaction mixture of step (a);
    (c) contacting the cooled reaction mixture with a dilute aqueous solution of an alkali or alkaline earth metal;
    (d) extracting the resulting mixture with an aliphatic or aromatic hydrocarbon;
    (e) combining the extracts of step (d);
    (f) heating the combined extracts of step (e) to a temperature in the range of 50° to 60° C.;
    (g) combining the heated combined extracts of step (f) with a precipitating agent; and
    (h) precipitating the product 1,2-5,6-diacetone-D-glucose.

14. The process according to claim 13, wherein X is selected from the group consisting of

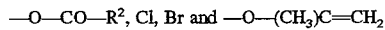

and $R^1$ and $R^2$ are independently methyl, ethyl, propyl, isopropyl, butyl, pentyl or hexyl.

15. The process according to claim 13, wherein the carboxylic acid derivative is acetic anhydride.

* * * * *